US 9,176,096 B2

(12) United States Patent
Goroshevskiy et al.

(10) Patent No.: US 9,176,096 B2
(45) Date of Patent: Nov. 3, 2015

(54) APPARATUS AND METHOD FOR METALLIC CONSTRUCTIONS ASSESSMENT (71) Applicants: Valerian Goroshevskiy, Moscow (RU); Svetlana Kamaeva, Moscow (RU); Igor Kolesnikov, Moscow (RU); Leonid Ivlev, Moscow (RU)

(72) Inventors: Valerian Goroshevskiy, Moscow (RU); Svetlana Kamaeva, Moscow (RU); Igor Kolesnikov, Moscow (RU); Leonid Ivlev, Moscow (RU)

( * ) Notice: Subject to any disclaimer, the term of this patent is extended or adjusted under 35 U.S.C. 154(b) by 323 days.

(21) Appl. No.: 13/920,216

(22) Filed: Jun. 18, 2013

(65) Prior Publication Data

US 2014/0368191 A1    Dec. 18, 2014

(51) Int. Cl.
*G01N 27/76* (2006.01)
*G01N 27/82* (2006.01)
*G01N 27/85* (2006.01)

(52) U.S. Cl.
CPC ............... *G01N 27/82* (2013.01); *G01N 27/85* (2013.01)

(58) Field of Classification Search
CPC ......... G01R 33/16; G01N 27/72; G01N 27/74
See application file for complete search history.

(56) References Cited

U.S. PATENT DOCUMENTS

| 4,316,146 | A  | * | 2/1982 | Jilken ........................... 324/209 |
| 8,723,673 | B2 | * | 5/2014 | Meiksin et al. ............... 340/566 |
| 2010/0005896 | A1 | * | 1/2010 | Miller et al. .................... 73/779 |
| 2011/0060568 | A1 | * | 3/2011 | Goldfine et al. .................. 703/6 |

* cited by examiner

*Primary Examiner* — Arleen M Vazquez
*Assistant Examiner* — Dominic Hawkins
(74) *Attorney, Agent, or Firm* — Nadya Reingand (57) ABSTRACT

A device for discovering, identification and monitoring of mechanical flaws in metallic structures is disclosed, based on magneto-graphic/magnetic tomography technique to identify stress-related defects. The device includes registration means that optimized for use with metallic structures of various types, shapes and sizes. Applications include a real-time quality control, monitoring and emergency alarms, as well structural repairs and maintenance work recommendations and planning. Examples of the device implementation include pipes for oil and gas industry monitoring, detection of flaws in rolled products in metallurgical industry, welding quality of heavy duty equipment such as ships, reservoirs. etc. It is especially important for loaded constructions, such as pressured pipes, infrastructure maintenance, nuclear power plant monitoring, bridges, corrosion prevention and environment protection.

20 Claims, 3 Drawing Sheets

APPARATUS AND METHOD FOR METALLIC CONSTRUCTIONS ASSESSMENT

CROSS-REFERENCE TO RELATED APPLICATION

This application is a continuation-in-part of the U.S. patent application Ser. No. 13/674,118 filed on Nov. 12, 2012, now allowed.

FIELD OF INVENTION

The present invention relates broadly to a device and method for continuous (extended) metallic structures inspection and monitoring for possible mechanical defects; in particular, to contact magnetic scanner device and method, using magnetic tomography for a real-time structural defects measurement and assessment.

BACKGROUND OF THE INVENTION

This invention can be used in various fields where constructions are tested for continuity defects in a contact fashion or combined with the remote method. Examples of device and method implementation may include pipes for oil and gas industry, detection of flaws in rolled products in metallurgical industry, welding quality of heavy duty equipment such as ships and reservoirs, etc. It is especially important for inspection of loaded constructions, such as pressured pipes, infrastructure maintenance, nuclear power plant monitoring, bridges, corrosion prevention and environment protection.

Similar to the modes of transportation like roads, railroads, and electric transmission lines, the pipelines have an important role in the nation's economy, belonging to the long linear assets. They typically cross large distances from the points of production and import facilities to the points of consumption. Like the other modes of transportation, pipelines require very large initial investment to be built, having long exploitation periods when properly maintained. Like any engineering structure, pipelines do occasionally fail. While pipeline rates have little impact on the price of a fuel, its disruptions or lack of capacity can constrain supply, potentially causing very large price spikes. That's why pipelines, such as ones used in the oil and gas industry, require regular inspection and maintenance before potentially costly failures occur.

The major causes of pipeline failures around the world are external interference and corrosion; therefore, assessment methods are needed to determine the severity of such defects when they are detected in pipelines. Pipeline integrity management is the general term given to all efforts (design, construction, operation, maintenance, etc.) directed towards ensuring continuing pipeline integrity.

Traditional contact methods of assessing the structural integrity typically complemented by flaw detection using in-line inspection (ILI), detecting and evaluating various metal defects organized by area (clusters), assessing their danger by calculating a level of stress-deformed state (SDS), and deciding on a permissible operating pressure with evaluated factor of repair (EFR), based on residual pipe wall thickness (for defects of "metal loss"—corrosion type).

As a contact technique, pigging devices has been used for many years to maintain larger diameter pipelines in the oil industry. Today, however, the use of smaller diameter pigging devices is increasing in many plants as plant operators search for increased efficiencies and reduced costs. Unfortunately, the ILI using intelligent pigging is unavailable for a wide range objects that require full disruptive inspection and significant spending on repair preparation. While the ILI method is suitable for the initial flaw detection, it is less efficient for the relative degree (ranking) of the risk-factor evaluation, as well as for defective pipeline serviceability calculation.

Pipe-line pigging device can detect the following types of defects: i) changing in geometry: dents, wavy surface, deformed shape of cross-section; ii) metal loss, having mechanical, technological or corrosion nature; material discontinuity: layering and inclusions; iii) cracks; iv) all types of welding defects.

Pipe-line pigging is a very expensive and labor-consuming method. The major limitation of this method is the fact that a large part of pipe-lines are not prepared for the pigging device operation, e.g. due to lack of input/output chambers for pig-flow device launching and pipe-line cleaning access, partially blocked pipe cross-section due to the welding artifacts, geometrical abnormalities and large slopes (small radius turns) of the pipe-line layout. In order to make the pipe-line pigging method possible, a significant preparation has to be done in advance, in particular, the high residual level magnetization (saturated magnetic fields) of the pipe-line has to be performed before using the pig-flow device. This causes future technical problems of the pipeline demagnetization that required for actual pipe repair after the pigging.

Moreover, the evaluation of the absolute values of mechanical flaws by pigging device is particular difficult due to the multiple additional factors that have to be taken into account, e.g. bearing capacity of the soil, local cyclical loads (temperature, etc.).

Aside of the remote methods, there are numerous contact non-destructive testing devices for access to the surface of the metallic construction (ultrasound-, eddy-current-, magnetic-powder-defectoscopy). The main disadvantages of such methods is the time-consuming procedure of surface preparation that reduces the scope of applicability and leads to high cost, low registration sensitivity and selectivity for hidden internal defects identification.

Typically, a pipeline company will have a thorough pipeline safety program that will include a routine for the identification of pipeline defects and review of pipeline integrity. Such a plan should include, but not be limited to i) a review of previous inspection reports by a third party expert; ii) excavation of sites identified by this review for visual examination of anomalies; iii) repairs as necessary; and iv) addressing factors in the failure and verify the integrity of the pipeline.

It is important to mention that the pipeline safety program can be only as effective as the interpretation of internal inspection reports.

There are several magnetographic devices that have been disclosed for non-destructive inspection of ferrous materials. In magneto-graphic inspection and defectoscopy the tested area of the material is placed in proximity to the magnetic medium. The changes of the surface-penetrating impede flux due to the material flows or deviations can be recorded. The resulting "magnetogram" of the material can provide the information about the location, size, and type of the defect or abnormality. In general, this information can be converted into the report about the quality of the material. Obtaining the magnetogram (magnetic picture) of the material in the course of the non-destructive inspection process is very challenging and typically requires additional forms of inspection, such as roentgenogram or an X-ray image.

For example, U.S. Pat. No. 4,806,862 (Kozlov) offers a contact method of magnetographic inspection of quality of materials, where a magnetic substance (such as liquid) is applied to be magnetized together with the tested material. According to the invention, the intensity of the magnetizing field is established by the maximum curvature of the surface of a drop of a magnetic fluid applied onto the surface of the material to be inspected, so that the resulting magnetogram can be used to assess the quality of the material.

In another magnetographic U.S. Pat. No. 4,930,026 (Kljuev), the flaw sensor for magnetographic quality inspection is disclosed, which includes a flaw detector and a mechanism for driving the magneto-sensitive transducer. During the scanning procedure, the magnetic leakage fluxes penetrate through the surface of the material in places where flaws occur, resulting in a magnetogram of the tested material.

There is another magnetic technique that has been proposed by U.S. Pat. No. 6,205,859 (Kwun) to improve the defect detection with magnetostrictive sensors for piping inspection. The method involves exciting the magnetostrictive sensor transmitter by using a relatively broadband signal instead of a narrow band signal typically used in order to avoid signal dispersion effects. The amplified detected signal is transformed by a short-time Fourier transform providing the identifiable signal patterns from either defects or known geometric features in the pipe such as welds or junctions.

There is a known contact device with two single-component collinear flux-gate magnetometers have been reported for the contact magnetometric monitoring and defects detection, RU 2062394. This device characterized by limited applicability due the slow data reception and processing and low sensitivity that makes impossible to detect minor deviations of stress-strain state (STS) from the background values, also leading to the low resolution threshold and a high false alarm rate.

The defect areas risk-factor criteria and ranking (such as material stress: F-value) is used for planning a required sequence of repair and maintenance steps. Such criteria were developed by comparing a risk-factor calculated using the defect geometry in calibration bore pits with a predicted risk-factor obtained by the remote magneto-metric data (i.e. comprehensive F-value of particular magnetic anomaly).

The deviations of F-value can be classified as follows: X1—for negligible defects (good technical condition of the metal); X2—for defects that require planned repairs (acceptable technical condition); X3—for defects that require immediate repairs (unacceptable, pre-alarm technical condition, alarm).

The absolute values X1-X3 of the F-value (comprehensive value of magnetic field anomaly) should be defined for each particular case, depending upon the following factors: i) Material (e.g. steel) type; ii) Topological location with the local background magnetic fields variation range, iii) Distance to the object (e.g. pipe-line installation depth), iv) General condition of the deformation-related tension within construction under testing, v) etc.

As a result, the only relative changes (variations) of the magnetic field can be evaluated for the given defective segment (relatively to the flawless segment), by comparing to its relative F-values. Thus, the very moment of the ultimate stress-limit crossing can be identified for each defective segment during the real operation (i.e. under pressure/loaded) condition. It can be done by monitoring the development of the defects within its F-value interval, namely, starting from the good technical condition X1 up until the yield-strength-limit approaching and material breakdown. It provides a real possibility to predict the defect's speed development, resulting in increased accuracy in priority order definition for upcoming maintenance steps.

The aforementioned techniques are not satisfactory to be used for efficient prediction in defects development timeline and not capable of providing a real-time alert about the strength-limits approaching, i.e. when probable construction failure is about to occur.

The closest remote technology to the disclosed invention is shown in RU 2264617 that describes the Magnetic Tomography (MT) technique. This technique includes a remote magnetic field vectors measurement in Cartesian coordinates with the movement of measuring device (magnetometer) along the pipe-line, the recording of the anomalies of magnetic field (on top of background magnetic field), processing of the data and report on found pipe-line defects with their localization shown in resulting magnetogram. The technique provides a good sensitivity, also capable of discovering the following types of defects: i) Changing in geometry: dents, wavy surface, deformed shape of cross-section; ii) Metal loss, having mechanical, technological or corrosion nature; material discontinuity: layering and inclusions; iii) Cracks; iv) Welding flaws, including girth weld defects. Moreover, such method provides a risk-factor ranking of the discovered pipe-line defects accordingly to material tension concentration (factor F). Accordingly this technique was taken as initial prototype for the disclosed technology.

MT determines the comparative degree of danger of defects by a direct quantitative assessment, of the stress-deformed condition of the metal. Conventional surveys only measure the geometrical parameters of a defect. Their subsequent calculations to assess the impact of the defect on the safe operation of the pipe do not take into consideration the stress caused by the defect. Therefore conventional surveys may fail to detect dangerously stressed areas of the pipe or, conversely, classify a defect as one which requires urgent attention when, in reality, the stress level may be low and the defect presents no immediate threat to the operation of the pipe. Since MT directly measures the stress caused by defects it is an inherently more accurate guide to the safe operation of the pipeline than conventional survey methods.

There are several methods for integrity assessment of extended structures (e.g. metallic pipes) that have been proposed in literature. Thus, U.S. Pat. No. 4,998,208 (Buhrow, et al) discloses the piping corrosion monitoring system that calculates the risk-level safety factor producing an inspection schedule. There is another method disclosed in U.S. Pat. No. 6,813,949 (Masaniello, et al.), which addresses a pipeline inspection system having a serviceability acceptance criteria for pipeline anomalies, specifically wrinkles, with an improved method of correlating ultrasonic test data to actual anomaly characteristics.

The main disadvantages of previous methods are: i) The scope of its application is limited by large-scale linear objects. Located at a considerable distance from each other, ii) Difficult real-time implementation of the device, iii) It is impossible to identify the location of individual defects, visualize and specify the exact position on the internal or external tested surfaces; iv) There is also a lack of visualization of the obtained information in a form of the resulting tomogram where all the locations of the defective segments with associated respective risk factors (absolute mechanical stress values) are shown.

There is a need in developing a combination of contact and remote techniques in order to increase sensitivity, resolution and visual representation of the stress-related anomalies within the structure, as well as a probability of operation failure (i.e. risk-factor).

SUMMARY OF THE INVENTION

A device for discovering, identification and monitoring of mechanical defects in extended metallic structure, such as pipe, a rail, a rolled metal product, a reservoir, a bridge, a vessel a cable, or electrical power transmission lines, is disclosed. The device includes a pulse generator being used to irradiate a part of the metallic structure, a sensor array registering a response from this part of the structure and a GPS. The sensor array is located in proximity of the structure and measures its magnetic field gradient at a distance of up to 20 cm from the structure without any surface preparation treatment. The sensor array includes a number of 3-component arrays, positioned along the 3 orthogonal dimensions. An analogue-to-digital converter digitizing the sensor signal which is wirelessly transmitted to the calculation unit.

A calculation unit exploits an inverse magnetostrictive (Villari) effect of changing material's magnetic susceptibility wider applied mechanical stress. Such changing results in gradient distribution of the magnetic field along the area of the structure that has a magnetic field anomaly. The distribution, in turn, reflects a presence and a value of the magnetic field anomaly at the given location. An absolute value of the mechanical stress, which corresponded to said anomaly, is further deducted, thus characterizing a mechanical defect of the structure, optionally using, a pre-determined information such as look-up tables, standards, thresholds or an alternative contact measurement such as a contact probe.

The sensor array functions without removing the non-metallic cladding of the structure, such as a concrete wall around a metallic pipe, for example. The sensor array measurements can also be performed from inside the pipeline.

The device detects foreign objects that are present in vicinity of the structure, measuring a relative distances and angles between themselves and the found anomaly. The discovered information is visualized by representing a topological map of the structure in real coordinates, showing simultaneously a structure layout, the foreign objects in vicinity, the location and calculated three-dimensional values of the mechanical stress.

The device is also capable of measuring a natural Earth's background magnetic field without engaging the pulse generator. Such measurement is subtracted from the sensor signal to improve accuracy of the anomaly(s) location.

The device is operated by the battery with a residual charge indicator to ensure a quality and reliability of the identification in the field conditions and can perform without interruption of the structure normal operation.

A method for discovering, identification and monitoring of mechanical defects of various nature, causing the concentration of mechanical tension in metallic structures, is also disclosed. The method includes an irradiating a part of the metallic structure with electromagnetic pulses, performing mechanical stress measurement of the metallic structure by a sensor array placed in proximity of the structure and producing a digitized sensor signal and digitizing the sensor signal. The method also includes analyzing the digitized signal in a calculation unit using the inverse magnetostrictive effect providing information about the presence and the value of the magnetic field anomaly at the given location of the structure. The method calculates absolute values of the mechanical stress around the anomaly, thus unveiling and characterizing the mechanical defect of the structure.

DETAILED DESCRIPTION OF THE PREFERRED EMBODIMENT

The present invention describes the contact magnetic scanner device that uses a magnetic tomography (MT) for contact magnetographic identification and analysis of mechanical flaws/defects, optimized for extended metallic constructions inspection. The invention can be used in combination with a non-contact identification. And can be applied to variety of extended metallic structures, such as a pipe, a rail, a rolled metal product, a reservoir, a bridge, a vessel a cable, or electrical power transmission lines.

The use of MT device has following advantages: 1) Applicable for the unpiggable pipelines or other objects where in-line inspection method is inapplicable; 2) the objects to be inspected include but not limited to: compressor stations pipelines, pipeline inclusions, water-supply pipelines in cities; 3) the use of MT device doesn't require any preparation of the pipeline for testing such as cleaning, opening the pipe, or stopping pipeline operation; 4) the use of MT device doesn't require magnetizing of the object's pipes; 5) MT device capable of detecting flaws of various types including long crack-like pipe-line defects and welding defects; 6) the use of MT device doesn't have limitation on the structure diameter, configuration and protective coatings, for example, change of pipe diameter/wall-thickness, turns and their directions, transported product (e.g. gas, oil, or water), inside pressure, pipeline protection e.g. cathodic protection, etc).

The MT device is capable to evaluate the degree of danger of defects by the level of concentration of mechanical tensions rather than defect geometry (e.g. length-width-depth) and particularly suitable for running a database on condition certification of objects of any length and any monitoring period.

The MT device implementation guarantees minimal customer resources use for monitoring preparation and repair works such as: i) reduces work volume and total costs of pipe access works; ii) greatly reduces time of full diagnostic—repair evaluation—repair planning—repair cycle; iii) gives pipe corrosion prognosis and estimates levels of tense-deformed state of the pipeline under current operating conditions.

The MT device application provides a remote metal flaws monitoring, which is particularly suitable for hidden ferromagnetic constructions of extended length.

Figure 1:
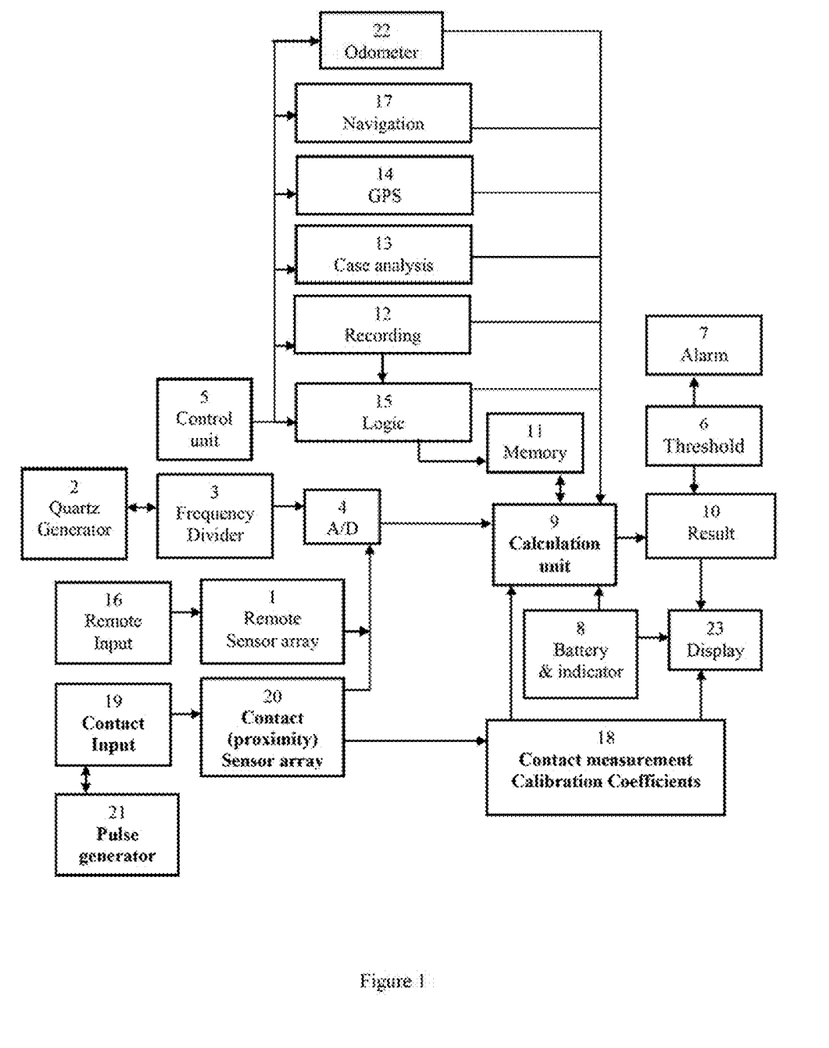
FIG. 1: The block-diagram of the device for discovering, identification and monitoring of mechanical defects in metallic structures using contact method, optionally, in combination with a non-contact technique.

The general combined block-diagram of the method is given in FIG. 1.

The magnetic tomography device is based on Using of the inverse magnetostrictive (Villari) effect—i.e. the changing of the material magnetic susceptibility under applied mechanical stress. Generally, such technique uses "natural" magnetization of the ferrous pipes by magnetic field of the Earth. The changing of magnetic susceptibility results in distribution of magnetic field gradient along the structure surface area under measurement, thus providing information about the presence and the value of the magnetic field anomaly at the given location of the structure.

The term "contact measurement", as used herein is defined as the measurement being used from a small distance from the surface of the structure under testing. For the preferred embodiment of the invention, such distance is defined as a small if it is less than 20 cm from the surface of the structure. Furthermore, for the preferred embodiment of the invention applying an additional (pulsed) magnetic field is used.

The term "remote measurement", as used herein is defined as the measurement being used from a substantial distance from the structure under testing. Unlike to the contact measurement (non-destructive or distractive), the remote sensor is not necessary located in a close proximity to the structure. For the preferred embodiment of the invention, the substantial distance have value of 1-50 m, making the disclosed device especially effective for testing structures located deep underground or underwater.

The remote measurement is capable of identifying, the anomalies by deviation of the Earth's magnetic field at each location from a background value, without applying an additional magnetic field during the measuring.

The contact measurement device is also capable localizing coordinates of foreign objects in vicinity of the structure and making, a linkage between the anomalies' locations and the foreign objects locations around. In the preferred embodiment of the invention, the device finds coordinates of foreign objects which can be present in vicinity of the structure and measures a distance/angle between those foreign objects and the structure's anomaly.

The both remote and contact measurements are further capable of localizing coordinates of the structure and detecting anomalies with localized coordinates within the extended metallic structure based on measuring a value of the Earth's magnetic field at multiple locations in vicinity of the structure.

The present invention discloses the Contact Magnetic Scanner—a device for the contact detection of the defects in metallic structures. The present invention effectively overcomes the aforementioned disadvantages of contact defect monitoring and detection.

Similarly to the remote method, the contact method at a given measurement point, the presence of the magnetic field anomaly and its magnitude (the local stress at the remote area) is determined based on a comparison between the increments (modules) of the Earth's magnetic field values (magnetic moments), Such calculation method is based on a dipole approximation of the remote stress-concentrator. The solution of the problem of the magnetic moment calculation results from a system of algebraic equations, which, for example, described in the patent U.S. Pat. No. 4,309,659.

The disclosed device expands the scope of device applications for different types of metallic structures (e.g. confined extended, small and large), ii) provided real-time operational means by including, data preprocessing and calibration, iii) increases the identification sensitivity of the defects located at the surface and within the volume of the object by including an additional pulse-magnetization unit, v) using a contact tomography technique in order to add 3D visualization capabilities using a 3D model of the tested object. The information visualization (display) unit of the device represents a topological map of the structure in real coordinates, showing; simultaneously a structure layout, the foreign objects in vicinity, the calculated values of a mechanical stress and the location of the found anomalies.

The disclosed device uses pre-determined information for structure anomaly identification and localizing. Such pre-determined information can be a look-up table, preset standards and thresholds, an alternative contact measurement, or combination of the above.

Moreover, the device can combine a contact and non-contact measurement increasing the reliability and accuracy of information about the necessary repair or stop alarm. It can be done using the risk-factor ranking tables based on the absolute values of stress, compared against the values from regulatory documentation (for particular object).

In the preferred embodiment of the invention, the device performs the identification of anomalies without interruption of the structure normal operation.

Increasing the efficiency of the method by applying a 3D visualization-assisted maintenance and repair schedule with the real values of mechanical stress) to the actual structural layout, such as a pipe-line integrated into the existing topology.

Such technological outcome can be achieved, mainly, due to the following innovative means: i) Contact (object surface) identification of the local defects and their respective risk-factors; ii) Comparing the remote measurement with ones obtained locally; iii) Comparing the resulting measurements against the values from regulatory. documentation (for particular object), iii) Graphical 3D visualization of the obtained information using the actual topological layout of the area and the structure in absolute geographical coordinates.

For the remote registration of magnetic field anomalies in extended metallic structures (such as a pipe) is performed in a predetermined coordinate system relatively to the structure (axis) with a known (fixed) remote sensor array aperture. The coordinates of each single measurement along the structure can be chosen accordingly to the cross-section size and burial depth of the (underground, underwater) structure. It results in the matrix distribution of magnetic field gradient along the structure surface area under each single measurement. The presence and the value of the magnetic field anomaly at the given location are derived from the comparison of different increments of the Earth's magnetic induction vector modulus.

Similarly to the remote measurements, the contact measurement also includes device to measure the magnetic field vector in Cartesian coordinates, by moving the registration device (magnetometer) along (above) the metallic structure (of arbitrary configuration, in general) and registration of the magnetic field anomalies, Such anomalies are calculated by a deviation from the background values (calculated using matrix transformations).

The contact device also connected the data recording unit and decoding system that provides conclusive information about the presence and location of the defects in the form of magnetograms that shows the location of the defective pipe sections and their degrees of risk.

Similarly to the remote measurements, the contact measurement of the extended object (such as pipeline) uses the recording of the magnetic field that is carried out in a pre-defined coordinate system at specifically defined measuring points by a set of sensors having a pre-selected aperture (base) $K2$. This aperture corresponds to the axis of the extended object with a measuring step $K1$.

The exact location of measurement points is defined from the diameter and underground depth (e.g. of the pipeline), using coefficients $K1$, $K2$ and $K3$, where: $K1$—is the measuring step (registration of the magnetic field induction) 0.2 m, for example, $K2$— the aperture (the base) of the sensors, chosen from the ratio $0.7\ D \le K\ 2 \le 1,4\ D$, where D—is the diameter of the structure (pipeline), $K3$—is the depth of the pipeline, or the shortest distance from the metallic construction to the surface, [m].

In the case of a non-linear (or small) extended object the contact registration c the magnetic field is carried out in a fixed coordinate system. In this case, registration is possible at different relative positions of the sensors and their arbitrary orientation with respect to the object (coplanar or collinear).

To verify the anomaly angular position along the structure (pipeline) circumference, the angular scanning step K1 should not larger than 30 degrees with the pre-defined distance between the sensors K2, to ensure the required accuracy of calculations.

The block-diagram of such device is shown in FIG. 1. with the reference to FIG. 1, the device for contact and, optionally, non-contact measurements comprises of a sensor array for remote measurements (1), a sensor array for proximity (contact) measurements (20), a quartz generator (2), a frequency divider (3), analogue-to-digital converter (A/D) (4), a control unit (5), a threshold unit (6), a light- and sound-alarm unit (7), a battery with a charge indicator (8), a calculation unit (9), a (resulting) information unit (10) with a display unit (23), a non-volatile memory unit (11), a recording unit (12), a case-analysis unit (13), a pulse generation lint (21), an odometer unit (23), a GPS unit (14), navigation unit (gyroscope/accelerometer) (17) and a logic unit (15). The device performs in a following manner.

The remote sensor array (1) registers induction gradients of the magnetic field (16) within construction under testing.

The proximity sensor array (20) registers induction gradients of the magnetic field (19), the gradients corresponding to reflections of the EM pulses from the structure; the EM pulses generated by the Pulse generator (21). The signal from the proximity sensor is used as a calibrating measurement.

By using A/D converter (4), the both digitized signals (remote and contact) are: i) inputted into calculation unit as a preliminary data; ii) recorded by the memory unit (11). The Quartz generator (2) controls the frequency of the A/D converter (4).

The control unit (5) through the logic unit (15) controls the case analysis unit (13) with predetermined database and lookup tables, the recording unit (12), the GPS unit (14), the navigation unit (17) and the memory unit (11).

The calculation unit (9) receives the information from units (12), (13), (14), (17), (20), (22) through the memory unit (11), controlled by logic unit (15).

The real-time information from (4) is compared with the information from the threshold unit (6). By these means, the visualization of the real-time data against the threshold values is provided, enabling the alarming (by the unit (7)) an operator about potentially dangerous operational conditions of the structure. The remaining charge of the battery (8) is monitored. The calculation unit (9) is responsible for the information processing, providing the information to the resulting, and visualization init (10).

The calculation unit (9) unit receives the digitized signal, uses the inverse magnetostrictive effect of changing of material magnetic susceptibility under applied mechanical stress resulting in gradient distribution of the magnetic field along an area of the structure that has a magnetic field anomaly, the distribution of magnetic field gradient providing an information about a presence and a value of the magnetic field anomaly at the given location of the structure and a mechanical stress, corresponded to the anomaly.

The calculation unit (9) further calculates absolute values of a mechanical stress around all found anomalies in the metallic structure using the measured values of the Earths magnetic field for each anomaly and applying the calibration coefficient As a result, the calculation unit is capable of identifying and localizing of said signal anomalies.

In one embodiment of the invention the calculation unit is located at a distance from the sensor array, and the digitized signal is transmitted to the calculation unit via wireless connection.

The measured magnetic field values from 2 inputs (16) and (19) local stress at the remote area are recorded at each measurement point, (both for contact and optional remote sensor independently), then further compared with other measurements within a respective segment of the metallic construction. By these means the anomalies (levels of stress-deformation) that deviate from the baseline magnetic field values are selected. Thus, the location of each stress-related deformation is derived from the maximum concentration value of the magnetic field after comparing it with the previous measurements.

The visualization unit has a 3-dimensional display means (23) in order to provide a 3-D representation of the density of magnetic field strength distribution, found detects and its risk-factors along with the topological (3D) map of the structure under testing.

The resulting and visualization init (10) also accommodates inputs from the threshold unit (6) and the light-/sound-alarm unit (7) which enables identification of the parameters' deviation from the background level, as well as (e.g. wirelessly) informing an operator about the deviation value in real-time, respectively.

Moreover, the resulting and visualization init (10) is capable of comparing the remote signals (16) with in-contact measurement (19) and producing a set of calibration coefficients in order to calibrate the resulting calculated data of found magnetic anomalies.

The situational case-analysis unit (13) enables the analysis of the information in the context of pre-determined technological information and schemes, which, in combination with the GPS unit (14), provides more accurate topological mapping.

In the preferable configuration of the device, a GPS sensor (14) is complemented by a navigation unit that includes gyroscope(s) and/or set of accelerometer(s) (17), and odometer unit (22) enabling the recording of the device's angle-positioning relatively to the extended metallic structure cross-section at each moment of the magneto-graphical measurements. The recorded angle-positioning data (including positioning, relatively to horizon) is used further to correct the magneto-graphical measurements due to structural bending/turning-related deviations.

Accordingly, the absolute coordinates of discovered defects relatively to the (visible) reference objects can be obtained with the following registration in the database during the equipment assessment report.

In the preferable configuration of the mentioned device, each sensor arrays (1) and (20) consist of a few 3-compenent arrays, positioned along the 3 orthogonal dimensions. Alternatively, each array includes a few single-component sensors, such as optically pumped quantum analyzers. Using the optically pumped quantum analyzers in the sensor array (1) allows higher flaw-detection accuracy in underground constructions, well-suited for detecting relatively small values of mechanical stress, and/or deeper underground installation.

Since die sensor array (1) and (20) can be rotated above the surface of the structure during the scanning procedure, it is possible to implement a polar coordinate system for detects detection, in combination with the data from the gyroscope/accelerometer unit (17).

The recording process is arranged in a discrete manner, enabling an independent storage and access for different recorded portions (memory segments) of the scanning.

In the preferable configuration of the disclosed device, the unit (9) calculates: i) magnetic field gradients distributed along the square area within the defined segment of the structure, ii) the values of the local mechanical stress within the defined segment of the structure.

The device allows identifying the location of defects using both in-contact and remote magnetic measurements.

Moreover, it expresses the calculations in real-time, also providing the visualization of the information in the form of tomograms with reference to the 3D model of the controlled object.

Moreover, the device provides automated evaluation of the defects risk factor at respective identified location, allows automatic processing, interpretation and archiving of non-destructive testing results.

In the alternative configuration of the disclosure, the calculation unit (9) can be realized similarly to the U.S. Pat. No. 4,309,659 patent.

Moreover, in the alternative configuration of the disclosure, the recording unit (12) can be realized similarly to the RU2037888 patent.

Figure 2:
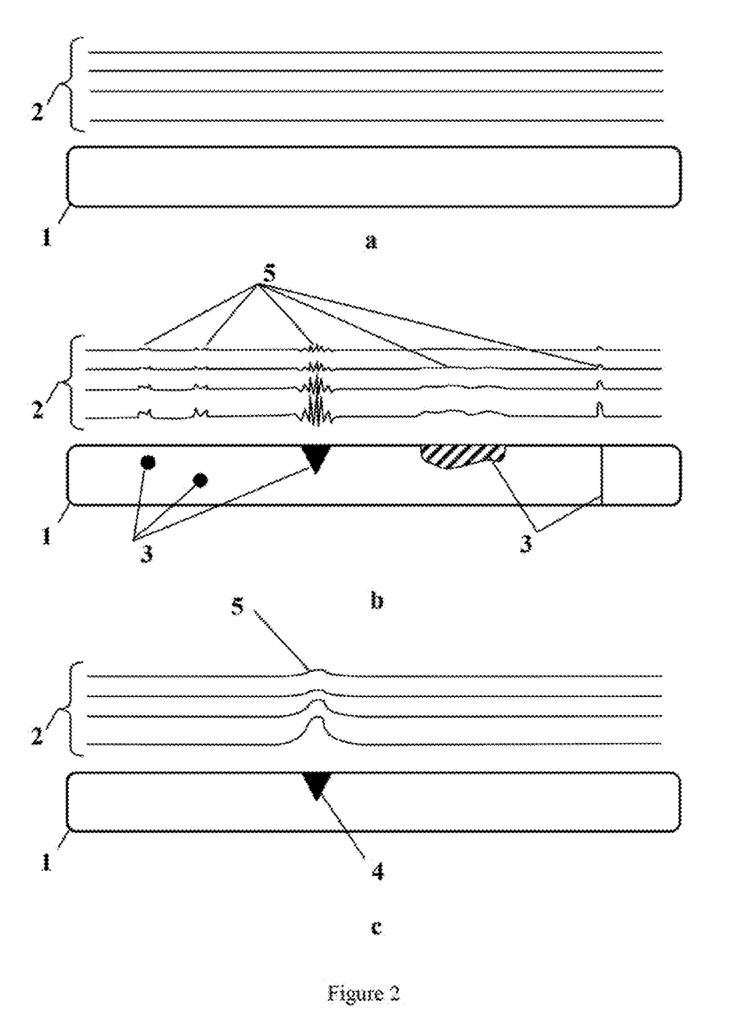
FIG. 2: A general principle of operation of the contact and non-contact magneto-graphic techniques used in metallic structure defects monitoring and integrity assessment.

The principle of operation of the device shown in FIG. 1. is explained further in FIG. 2. The FIG. 2a shows the structure (1) without defects, with the preliminary magnetic tomography charts (magnetogram) (2) showing the measured background (calibrated to zero) level of magnetization. The FIG. 2b shows the same structure (1) with the potential defects (3), (4) corresponded to the deviations of the tomography charts (5). The FIG. 2c show the same structure (1) with the processed tomography charts (5), showing the location of the defect (4) that require an immediate attention (unacceptable, pre-alarm technical condition, alarm), based on the local mechanical stress value estimate.

As mentioned before, the magnetogram (2) attributes and characterizes the section of the structure by registering and analyzing changes in the magnetic field of the structure such as pipeline. These changes are related to stress, which, in turn, is related to defects in the metal and insulation. Magnetic measurements data is collected from the surface and includes the detected anomalies. Such detected anomalies are function of a local stress and/or local mechanical tension and structural changes in the metal. Moreover, a post-processing of this experimental data enables the visualization of the flaws in the structure.

The device can operate on the metallic structure which is covered by a non-metallic cladding and the sensor array performs the measurement without removing the cladding, for example, when the metallic structure is a pipeline and the cladding is a pipeline insulation cover. Moreover, the device (sensor array) is capable of performing measurements from inside the structure, such as a pipeline.

The described MT device does not measure the dimensions of geometric defects alone, but, instead, provides a stress measurement caused b these defects and identifies their character, location and orientation in accordance with the location and orientation of the area of stress. Linear and angular coordinates of flaws in the metal and coating are have been experimentally defined within a tolerance of +/−0.25 m.

The device explained by FIG. 1 and FIG. 2 can effectively identify and analyze the magnetic field anomalies in areas with stress concentrators caused by: i) defects or changes in structural conditions (such as metal loss, cracks, dents, lamination and inclusions); ii) erosion, seismic activity, or third-party damage.

Figure 3:
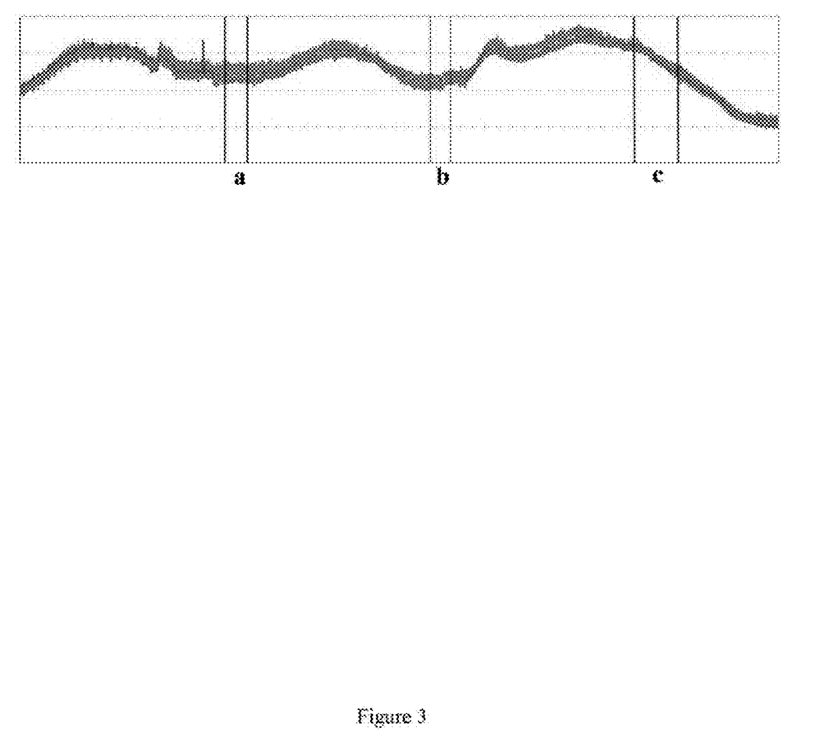
FIG. 3: An example of a single magneto-graphic measurement. The diagram represents the three areas of a magnetic field anomalies (a), (b) and (c) corresponding to the respective local mechanical stresses. The area (c) shows the evidence of the metal stress yielding-limit crossing.

FIG. 3 shows the example of a single magneto-graphic measurement. The diagram represents the three areas of a magnetic field anomalies (a), (b) and (c) corresponding to the respective local mechanical stresses. The area (c) shows the evidence of the metal stress yielding-limit crossing.

In parallel, the in-contact (proximity) defectoscopy has been performed at the location (c). The actual dimensions of defects (cracks and corrosion) have been evaluated. The magnetographic device calibration has been done based on a difference between the measured signal (versus background) and the actual parameters of the defect(s) found. Then, the calibrated values of the anomalies have been used as a criterion. For this particular case, the calibrated values appeared to be 3-10 times higher comparing to the background signal value. The follow-up magnetographic measurements ha been performed in a real-time.

The presented MT device helps to plan necessary structural maintenance procedures and define their priorities. The device is particularly efficient when the magneto-graphic material (Magnetic Tomography) inspection is applied to extended metallic constructions, revealing its flaws against the topological map of the structure.

Moreover, the device enables direct monitoring of the defective construction segments with still acceptable technical conditions. It allows a long-term database support for the follow up monitoring, certification, prognosis and operational timeline for the structure.

In the preferred embodiment of the invention the non-destructive detection of anomalies in the structure is performed using magnetographic technique such as MT.

The main goals of the present invention are: i) to increase the method's applicability area; ii) to increase the accuracy of the priority scheduling for required maintenance and repair procedures; iii) to broaden the spectrum of the potentially scheduled repair procedures, based on the additional data.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A device for discovering, identification and monitoring of mechanical defects in metallic structures, comprising:

an electromagnetic pulse generator, said generator irradiating a part of the metallic structure with electromagnetic radiation;

a sensor array registering a response of the part of the metallic structure on the irradiated electromagnetic radiation;

the sensor array located in proximity of the structure, performing magnetic field distribution measurement of the metallic structure and producing a sensor signal;

an analogue-to-digital converter digitizing the sensor signal;

a calculation unit receiving the digitized signal, the calculation unit uses the inverse magnetostrictive effect, the effect of changing of material magnetic susceptibility under applied mechanical stress, the changing of magnetic susceptibility resulting in gradient distribution of the magnetic field along an area of the structure that has a magnetic field anomaly, the distribution of magnetic field gradient providing an information about a presence and a value of the magnetic field anomaly at the given location of the structure and a mechanical stress, corresponded to said anomaly; and the calculation unit calculating an absolute value of the mechanical stress around the anomaly, thus unveiling a mechanical defect of the structure and characterizing it.

2. The device of the claim 1, wherein the metallic structure is covered by a non-metallic cladding and the sensor array performs the measurement without removing the cladding.

3. The device of the claim 2, wherein the metallic structure is a pipeline and the cladding, is a pipeline insulation cover.

4. The device of the claim 2, wherein the non-metallic cladding is a concrete wall.

5. The device of the claim 1, wherein the sensor array performs the measurement from a distance of up to 20 cm from a surface of the structure and without a preparatory treatment of the surface.

6. The device of the claim 1, wherein the structure is a pipeline and the sensor array performs measurements from inside the pipeline.

7. The device of the claim 1, further localizing coordinates of foreign objects which can be present in vicinity of the structure and a distance and an angle between those foreign objects and the structure anomaly.

8. The device of the claim 7, further comprising an information visualization unit to represent a topological map of the structure in real coordinates, showing simultaneously a structure layout, the foreign objects in vicinity, the calculated values of a mechanical stress and the location of the anomaly.

9. The device of the claim 1, wherein the sensor array comprises a few 3-component arrays, positioned along the 3 orthogonal dimensions.

10. The device of the claim 9, wherein the sensor signal provides information being sufficient to form a 3-dimensional image of the defect with localized coordinates.

11. The device of the claim 1, performing additionally the Earth's magnetic field measurement when the pulse generator is turned off and producing a background signal;
then subtracting the background signal from the sensor signal thus improving an accuracy of the anomaly location.

12. The device of the claim 1, wherein the extended metallic structure is a pipe, a rail, a rolled metal product, a reservoir, a bridge, a vessel a cable, or electrical power transmission lines.

13. The device of the claim 1, wherein the calculation unit is located at a distance from the sensor array, and the digitized signal is transmitted to the calculation unit via wireless connection.

14. The device of the claim 1, wherein the device being operated by the battery for performing the anomaly identification in field, the battery having residual charge indicator to ensure a quality and reliability of the identification.

15. The device of the claim 1, wherein identifying and localizing anomaly includes a pre-determined information.

16. The device of claim 15, wherein the pre-determined information is look-up tables, standards and thresholds.

17. The device of the claim 1, further comprising a Global Positioning Sensor measurement of the structure location and calibration of anomalies location.

18. The device of the claim 1, wherein the identification of anomalies is performed without interruption of the structure normal functioning.

19. The device of the claim 1, further comprising a remote sensor array localizing coordinates of the structure and detecting anomalies with localized coordinates within the extended metallic structure by using a non-contact remote technique based on measuring a value of the Earth's magnetic field at multiple locations in vicinity of the structure and identifying the anomalies by deviation of the Earth's magnetic field at each location from a background value, without applying an additional magnetic field during the measuring.

20. A method for discovering, identification and monitoring of mechanical defects of various nature causing a concentration of mechanical tension in metallic structures, comprising:
irradiating a part of the metallic structure with electromagnetic pulses;
registering a response of the part of the metallic structure on the irradiated electromagnetic radiation by a sensor array placed in proximity of the structure,
producing a sensor signal and digitizing the sensor signal;
analyzing the digitized signal in a calculation unit, the calculation unit using the inverse magnetostrictive effect, the effect of changing of material magnetic susceptibility under applied mechanical stress, the changing of magnetic susceptibility resulting in distribution of magnetic field gradient along an anomaly area, the distribution of magnetic field gradient providing an information about the presence and the value of the magnetic field anomaly at the given location of the structure and a mechanical stress; and
calculating absolute values of the mechanical stress around the anomaly, thus unveiling the mechanical defect of the structure and characterizing it.

* * * * *